United States Patent
Zhang et al.

(10) Patent No.: US 12,005,156 B2
(45) Date of Patent: Jun. 11, 2024

(54) BERBERINE/MINERALIZED COLLAGEN-BASED COMPOSITE MEMBRANE AND PREPARATION METHOD AND APPLICATION THEREOF

(71) Applicant: WEIFANG MEDICAL UNIVERSITY, Shandong (CN)

(72) Inventors: Weifen Zhang, Shandong (CN); Jian Zhang, Shandong (CN); Jingjing Zhang, Shandong (CN); Dejun Ding, Shandong (CN); Xiuwen Guan, Shandong (CN); Linlin Hu, Shandong (CN); Yuhan Zhang, Shandong (CN)

(73) Assignee: WEIFANG MEDICAL UNIVERSITY, Shandong (CN)

( * ) Notice: Subject to any disclaimer, the term of this patent is extended or adjusted under 35 U.S.C. 154(b) by 526 days.

(21) Appl. No.: 17/413,390

(22) PCT Filed: Apr. 2, 2021

(86) PCT No.: PCT/CN2021/085258
§ 371 (c)(1),
(2) Date: Jun. 11, 2021

(87) PCT Pub. No.: WO2022/105091
PCT Pub. Date: May 27, 2022

(65) Prior Publication Data
US 2023/0355837 A1 Nov. 9, 2023

(30) Foreign Application Priority Data
Nov. 23, 2020 (CN) .......................... 202011317356

(51) Int. Cl.
| | |
|---|---|
| A61L 27/26 | (2006.01) |
| A61F 2/30 | (2006.01) |
| A61L 27/20 | (2006.01) |
| A61L 27/24 | (2006.01) |
| A61L 27/48 | (2006.01) |
| A61L 27/58 | (2006.01) |
| D01D 5/00 | (2006.01) |
| D04H 1/4282 | (2012.01) |
| D04H 1/435 | (2012.01) |
| D04H 1/728 | (2012.01) |
| D04H 3/007 | (2012.01) |
| D04H 3/011 | (2012.01) |
| D04H 3/16 | (2006.01) |
| D06M 15/03 | (2006.01) |
| D06M 23/10 | (2006.01) |
| D06M 101/18 | (2006.01) |
| D06M 101/32 | (2006.01) |

(52) U.S. Cl.
CPC .......... *A61L 27/26* (2013.01); *A61F 2/30965* (2013.01); *A61L 27/20* (2013.01); *A61L 27/24* (2013.01); *A61L 27/48* (2013.01); *A61L 27/58* (2013.01); *D01D 5/0038* (2013.01); *D01D 5/0084* (2013.01); *D04H 1/4282* (2013.01); *D04H 1/435* (2013.01); *D04H 1/728* (2013.01); *D04H 3/007* (2013.01); *D04H 3/011* (2013.01); *D04H 3/16* (2013.01); *D06M 15/03* (2013.01); *D06M 23/10* (2013.01); *A61L 2400/12* (2013.01); *A61L 2430/02* (2013.01); *D06M 2101/18* (2013.01); *D06M 2101/32* (2013.01); *D10B 2321/12* (2013.01); *D10B 2331/041* (2013.01); *D10B 2509/00* (2013.01)

(58) Field of Classification Search
None
See application file for complete search history.

(56) References Cited

U.S. PATENT DOCUMENTS

| | | | | |
|---|---|---|---|---|
| 5,776,193 A | * | 7/1998 | Kwan | ................ A61L 24/0036 623/23.61 |
| 6,300,315 B1 | * | 10/2001 | Liu | ...................... A61K 9/7007 424/443 |

FOREIGN PATENT DOCUMENTS

| | | | | |
|---|---|---|---|---|
| CN | 102028969 A | * | 4/2011 | |
| CN | 111359005 A | * | 7/2020 | ........... A61L 24/001 |

OTHER PUBLICATIONS

Weisgerber et al. "Evaluation of multi-scale mineralized collagen—polycaprolactone composites for bone tissue engineering," Journal of the Mechanical Behavior of Biomedical Materials 61:318-327, 2016 (Year: 2016).*

(Continued)

Primary Examiner — David J Blanchard
Assistant Examiner — Alissa Prosser
(74) Attorney, Agent, or Firm — TAROLLI, SUNDHEIM, COVELL & TUMMINO L.L.P.

(57) ABSTRACT

The invention relates to bone repair and more specifically to a berberine/mineralized collagen-based composite membrane, a preparation method, and an application thereof. The composite membrane includes a berberine nanofiber membrane and a mineralized collagen membrane disposed on a unilateral surface of the berberine nanofiber membrane. The mineralized collagen with biomimetic mineralization capacity is combined with a Chinese materia medica monomer, berberine, the resulting bilayer composite membrane has a better effect on promoting osteogenesis In addition, a novel dosage form of berberine is constructed. An electrospinning method prepares a berberine nanofiber membrane. The berberine nanofibers are received by the mineralized collagen membrane, or after the berberine nanofiber membrane is obtained, a mineralized collagen membrane is prepared by applying on the surface of the berberine nanofiber membrane.

8 Claims, 2 Drawing Sheets

(56) References Cited

OTHER PUBLICATIONS

Kim et al. "Electrospinning of PCL/PVP blends for tissue engineering scaffolds," Journal of Materials Science: Materials in Medicine 24:1425-1442, 2013 (Year: 2013).*
Bao et al. "A berberine-loaded electrospun poly-(e-caprolactone) nanofibrous membrane with hemostatic potential and antimicrobial property for wound dressing," Journal of Biomedical Nanotechnology 9:1173-1180, 2013 (Year: 2103).*
Li et al. "Flexible bipolar nanofibrous membranes for improving gradient microstructure in tendon-to-bone healing," Acta Biomaterialia 61:204-216, 2017 (Year: 2017).*
Google translation CN 111359005 A, printed 2024 (Year: 2024).*
Google translation CN 111068101 A, printed 2024 (Year: 2024).*
Google translation CN 102028969 A, printed 2024 (Year: 2024).*

* cited by examiner

BERBERINE/MINERALIZED COLLAGEN-BASED COMPOSITE MEMBRANE AND PREPARATION METHOD AND APPLICATION THEREOF

RELATED APPLICATIONS

The present invention is a U.S. National Stage under 35 USC 371 patent application, claiming priority to Serial No. PCT/CN2021/085258, filed on 2 Apr. 2021; which claims priority of CN 202011317356.X, filed on 23 Nov. 2020, the entirety of both of which are incorporated herein by reference.

TECHNICAL FIELD

The present disclosure relates to the technical field of bone repair, and specifically relates to a berberine/mineralized collagen-based composite membrane as well as a preparation method and an application thereof.

BACKGROUND

Bone defect is one of common clinical diseases, usually caused by injuries, tumors and infections. Bone defect has a high incidence rate, it is difficult to heal if the defect is beyond a certain range, and an external force is required to repair the bone tissue. At present, there are mainly three means commonly used in clinic for bone repair, including autogenous bone grafting, allogeneic bone grafting and artificial bone material implantation. After the repair of bone tissue, drugs are usually needed to promote the growth of bone tissue and guide the regeneration of bone defects.

Berberine is a kind of natural alkaloid common in clinic, and widely exists in roots of goldthread, Goldenseal, *Berberis vulgaris, Berberis* and other Chinese medicinal herbs. It has been used for more than two thousand years. It has extensive pharmacological activities, including resistance to pathogenic microorganisms, anti-tumor, decreasing blood glucose, protecting heart and cerebral vessels, anti-inflammation, anti-Alzheimer disease, alleviating symptoms of intestinal diseases, promoting osteogenesis and anti-osteoporosis, and so on. At the same time, some other studies have found that, berberine can inhibit the formation and activity of osteoclasts, and simultaneously promote the differentiation of osteoblasts; moreover, berberine has advantages of few side effects, moderate effects, and low cost, so its clinical application has received more and more attention. In traditional Chinese medicine prescriptions, berberine is an effective constituent in many orthopedic prescriptions (such as Er-xian decoction and San-huang restorative). Berberine is used in clinic commonly in two dosage forms of tablets and injections. Tablets for oral use have the defects of poor absorption and low bioavailability; and the drug metabolism of injection preparations is fast after injection, thus requiring frequent injections; in addition, too large doses can cause anaphylactic shock, drug eruption and other untoward effects.

SUMMARY

The present disclosure is intended to provide a berberine/mineralized collagen-based composite membrane as well as a preparation method and an application thereof. The present disclosure constructs a novel dosage form of berberine, the provided berberine/mineralized collagen-based composite membrane has a high bioavailability and excellent osteogenic properties, is convenient to use and not easy to cause adverse effects.

To achieve the above object, the present disclosure provides the following technical solutions:

A berberine/mineralized collagen-based composite membrane, comprising a berberine nanofiber membrane and a mineralized collagen membrane disposed on a unilateral surface of the berberine nanofiber membrane;

the berberine nanofiber membrane comprises components of the following mass fractions: 20-65% of polycaprolactone, 18-80% of water-soluble compounds, and berberine≤0.1%; the water-soluble compounds comprise one or more of polyvinylpyrrolidone, tannin, proteins and polysaccharides;

the mineralized collagen membrane comprises components of the following mass fractions: 15-90% of chitosan, and 10-85% of mineralized collagen.

Preferably, the diameter of the fibers in the berberine nanofiber membrane is 700-800 nm.

Preferably, the thickness of the berberine nanofiber membrane is 0.1-0.4 mm, and the thickness of the mineralized collagen membrane is 0.1-0.4 mm.

Preferably, the chitosan has a molecular weight of 12-50 kDa.

The present disclosure provides a preparation method of the berberine/mineralized collagen-based composite membrane in the above solution, comprising the following steps:

(1) mixing the chitosan, the mineralized collagen with a glacial acetic acid solution, the resulting mineralized collagen suspension is cast into a film, to get the mineralized collagen membrane; and (2) mixing the polycaprolactone, the water-soluble compounds, the berberine with a solvent to get an electrospinning solution, the electrospinning solution is electrospun and the electrospun fibers are received by the mineralized collagen membrane, to get the berberine/mineralized collagen-based composite membrane; and alternatively, the berberine/mineralized collagen-based composite membrane is prepared by a method comprising the following steps:

(i) mixing the polycaprolactone, the water-soluble compounds, the berberine with a solvent to get an electrospinning solution, and the electrospinning solution is electrospun to get the berberine nanofiber membrane; and (ii) mixing the chitosan, the mineralized collagen with a glacial acetic acid solution, and the resulting mineralized collagen suspension is coated on the surface of the berberine nanofiber membrane and dried to get the berberine/mineralized collagen-based composite membrane.

Preferably, in the mineralized collagen suspension of the step (1) and the step (ii), the mass fraction of chitosan is 0.5-6%, and the mass fraction of the mineralized collagen is 0.1-2%.

Preferably, the method for casting into a film in the step (1) is as below: the mineralized collagen suspension is poured into a mould and dried to get the mineralized collagen membrane; the drying temperature is 25-45° C., and the time is 2-5 h.

Preferably, the mixing processes in the step (2) and the step (i) are as below: berberine is dissolved in a solvent to get a berberine solution, then polycaprolactone and the water-soluble compounds are respectively dissolved in the berberine solution to get a polycaprolactone-berberine solution and a water-soluble compound-berberine solution; the polycaprolactone-berberine solution and the water-soluble compound-berberine solution are mixed to get the electrospinning solution.

Preferably, the mass concentration of polycaprolactone in the polycaprolactone-berberine solution is 5-15%; the mass concentration of the water-soluble compounds in the water-soluble compound-berberine solution is 10-30%; the volume ratio of the polycaprolactone-berberine solution to the water-soluble compound-berberine solution is 7:(2-4); the concentration of berberine in the electrospinning solution is 5-50 μmol/L; the solvent is a mixed solvent of trichloromethane and methanol.

Preferably, the volume ratio of trichloromethane to methanol in the mixed solvent is (2-4):1.

Preferably, in the step (2) and the step (i), the parameters for electrospinning include: the liquid flow rate is 0.01-0.1 mm/min, the receiving distance is 10-15 cm, and the forward voltage is 10-15 kV.

The present disclosure also provides an application of the above berberine/mineralized collagen-based composite membrane or the berberine/mineralized collagen-based composite membrane prepared by the above preparation method in the preparation of drugs for bone repair.

The present disclosure also provides a method of using the above berberine/mineralized collagen-based composite membrane or the berberine/mineralized collagen-based composite membrane prepared by the above preparation method as membrane materials for osteogenesis, which is as below: covering the berberine/mineralized collagen-based composite membrane on the surface of bone injuries.

The present disclosure provides a berberine/mineralized collagen-based composite membrane, comprising a berberine nanofiber membrane and a mineralized collagen membrane disposed on a unilateral surface of the berberine nanofiber membrane; the berberine nanofiber membrane comprises components of the following mass fractions: 20-65% of polycaprolactone, 18-80% of water-soluble compounds, and berberine≤0.1%; the mineralized collagen membrane comprises components of the following mass fractions: 15-90% of chitosan, and 10-85% of mineralized collagen. In the present disclosure, the berberine nanofiber membrane and the mineralized collagen membrane are combined together, to get a bilayer composite membrane, where the mineralized collagen has biomimetic mineralization capacity, it has a self-assembled chemical structure of nanometer calcium phosphate and collagen molecules, thus having a biomimetic mineralization structure and mechanical properties similar to the nature bone of human body, excellent biocompatibility and osteogenic activity, as well as biodegradability; berberine can effectively inhibit the formation of osteoclasts and promote the differentiation of osteoblasts with few side effects; moreover, berberine exists in the form of nanofiber membrane, where the diameter of nanofibers is smaller than cells, so that they can simulate the structural and biological functions of natural extracellular matrix; in addition, nanofibers are similar to most tissues or organs of human, for example periosteum, in terms of forms and structures, thus having excellent biocompatibility, easy to be absorbed and highly safe. In the present disclosure, the mineralized collagen with biomimetic mineralization capacity is combined with a Chinese materia medica monomer, berberine, the resulting composite membrane has a better effect on promoting osteogenesis; in addition, a novel dosage form of berberine is constructed, solving the disadvantages of traditional berberine dosage forms such as low bioavailability, frequent administration, serious adverse effects and so on.

Additionally, the present disclosure employs polycaprolactone and water-soluble compounds for carrying drugs. Polycaprolactone is a good material for preparing nanofiber membrane, but it has poor hydrophilicity and degrades slowly. Water-soluble compounds are added in the present disclosure to promote the degradation of polycaprolactone in the body. The water-soluble compounds used in the present disclosure all have excellent film-forming ability and biocompatibility. In the present disclosure, polycaprolactone and water-soluble compounds are combined to carry berberine, which can improve the promoting effect of the composite membrane on bone repair on the premise of safety.

Chitosan is added in the mineralized collagen membrane of the present disclosure. Chitosan has the characteristics of nontoxicity, biodegradablity, biological versatility and biocompatibility, so it can enhance the differentiation of precursor bone cells and promote bone formation. However, due to the lack of inorganic structure of bone tissue, a single component of chitosan has no biological activity of bone bonding, so it cannot be directly used for bone tissue repair. In the present disclosure, chitosan is combined with the mineralized collagen as an auxiliary material, so that the biological properties of the two materials are complementary to each other, thus improving the bone repair effect of the composite membrane.

The results of examples show that, the berberine/mineralized collagen-based composite membrane of the present disclosure can significantly promote the proliferation of MC3T3-E1 cells.

The present disclosure also provides a preparation method of the berberine/mineralized collagen-based composite membrane in the above solution. In the present disclosure, an electrospinning method is used to prepare the berberine nanofiber membrane, the mineralized collagen membrane is used to receive the berberine nanofibers, or after the berberine nanofiber membrane is obtained, a mineralized collagen membrane is prepared by applying on the surface of the berberine nanofiber membrane. The preparation method of the present disclosure is simple, low in cost, and easy for industrial production.

DETAILED DESCRIPTION

Figure 1:
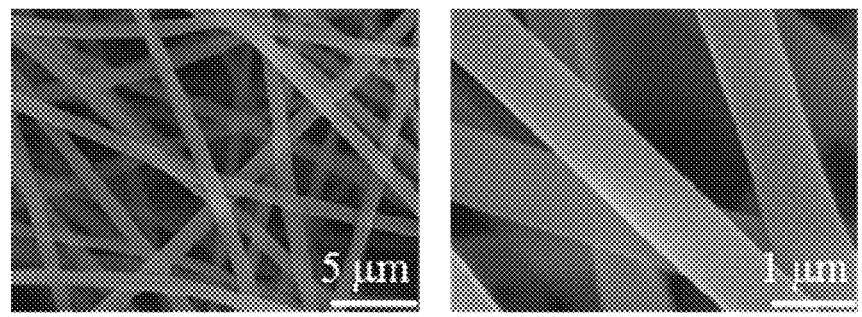
FIG. 1 is a scanning electron micrograph of the berberine nanofiber membrane prepared in example 7.

The present disclosure will be further illustrated in combination with the embodiments and attached drawings below.

The present disclosure provides a berberine/mineralized collagen-based composite membrane, comprising a berberine nanofiber membrane and a mineralized collagen membrane disposed on a unilateral surface of the berberine nanofiber membrane.

In the present disclosure, the berberine nanofiber membrane comprises components of the following mass fractions: 20-65% of polycaprolactone (PCL), preferably 25-60%, and more preferably 30-55%; 18-80% of water-soluble compounds, preferably 20-70%, and more preferably 30-60%; berberine≤0.1%, preferably 0.001-0.08%, and more preferably 0.002-0.05%. The water-soluble compounds comprise one or more of polyvinylpyrrolidone (PVP), tannin, proteins and polysaccharides, preferably polyvinylpyrrolidone. The diameter of the fibers in the berberine nanofiber membrane is preferably 700-800 nm, more preferably 300-800 nm.

In the present disclosure, the mineralized collagen membrane comprises components of the following mass fractions: 15-90% of chitosan, preferably 20-85%, more preferably 35-80%, and most preferably 71.43%; and 10-85% of mineralized collagen, preferably 20-80%, more preferably 25-60%, and most preferably 28.57%. The molecular weight of chitosan is preferably 12-50 kDa, more preferably 12-40 kDa, and further preferably 12-16 kDa.

In the present disclosure, the thickness of the berberine nanofiber membrane is preferably 0.1-0.4 mm, and the thickness of the mineralized collagen membrane is preferably 0.1-0.4 mm.

The present disclosure also provides two preparation methods of the berberine/mineralized collagen-based composite membrane in the above solution, which are remarked as Method I and Method II and illustrated as below respectively:

The Method I includes the following steps:
(1) Mixing the chitosan, the mineralized collagen with a glacial acetic acid solution, the resulting mineralized collagen suspension is cast into a film, to get the mineralized collagen membrane;
(2) Mixing the polycaprolactone, the water-soluble compounds, the berberine with a solvent to get an electrospinning solution, the electrospinning solution is electrospun and the electrospun fibers are received by the mineralized collagen membrane, to get the berberine/mineralized collagen-based composite membrane.

In the present disclosure, chitosan, mineralized collagen and a glacial acetic acid solution are mixed to get the mineralized collagen suspension. In the present disclosure, the volume fraction of glacial acetic acid in the glacial acetic acid solution is preferably 1%, and the solvent is pure water. In the present disclosure, glacial acetic acid is added to promote the dissolution of chitosan. In the present disclosure, it is preferable to dissolve chitosan in a glacial acetic acid solution firstly by magnetic stirring, and then add the mineralized collagen for ultrasonic treatment and stirring successively to get a mineralized collagen suspension. In the present disclosure, the mass fraction of chitosan in the mineralized collagen suspension is preferably 0.5-6%, more preferably 1.5-4%, and most preferably 2%; and the mass fraction of the mineralized collagen is preferably 0.1-2%, more preferably 0.5-1%, and most preferably 0.8%.

In the present disclosure, after the mineralized collagen suspension is obtained, it is cast into a film to get the mineralized collagen membrane. In the present disclosure, the method for casting into a film is preferably as below: the mineralized collagen suspension is poured into a mould and dried to get the mineralized collagen membrane; the drying temperature is preferably 25-45° C., more preferably 37° C., and the time is preferably 2-5 h, and more preferably 2-4 h; and the mould is preferably a culture dish. In specific examples of the present disclosure, it is preferable to pour 5 mL of the mineralized collagen suspension into a culture dish with a diameter of 10 cm (or scaling up to prepare mineralized collagen membranes with larger areas), and then spread out and dry.

In the present disclosure, polycaprolactone, water-soluble compounds, berberine and a solvent are mixed to get the electrospinning solution. In the present disclosure, the solvent is preferably a mixed solvent of trichloromethane and methanol, and the volume ratio of trichloromethane to methanol in the mixed solvent is preferably (2-4):1, and more preferably 3:1.

In the present disclosure, the mixing processes are preferably as below: berberine is firstly added into a solvent to get a berberine solution, then polycaprolactone and the water-soluble compounds are respectively dissolved in the berberine solution to get a polycaprolactone-berberine solution and a water-soluble compound-berberine solution; the polycaprolactone-berberine solution and the water-soluble compound-berberine solution are mixed to get the electrospinning solution. In the present disclosure, the mass concentration of polycaprolactone in the polycaprolactone-berberine solution is preferably 5-15%, and more preferably 10-12%; the mass concentration of the water-soluble compounds in the water-soluble compound-berberine solution is preferably 10-30%, and more preferably 25-30%; the volume ratio of the polycaprolactone-berberine solution to the water-soluble compound-berberine solution is 7:(2-4), and more preferably 7:3; the concentration of berberine in the electrospinning solution is preferably 5-50 μmol/L, and more preferably 10-20 μmol/L.

In the present disclosure, after the electrospinning solution is obtained, it is electrospun and the electrospun fibers are received by the mineralized collagen membrane to get the berberine/mineralized collagen-based composite membrane. In the present disclosure, an injector is preferably used to suck the electrospinning solution, then the injector is placed on the ejector of the electrospinning device, the mineralized collagen membrane is coated on the surface of the receiver, and then the electrodes are connected to start electrospinning. In the present disclosure, the model of the needle used for electrospinning is preferably 20 G, and the receiver is preferably a steel sheet coated with aluminum foil. In specific examples of the present disclosure, the mineralized collagen membrane is preferably located at the place closest to the electrospinning needle as a straight line, and the volume of solution used for electrospinning each time is 10 mL.

In the present disclosure, the parameters for electrospinning preferably include: the liquid flow rate is 0.01-0.1 mm/min, and more preferably 0.03-0.05 mm/min; the receiving distance is 10-15 cm, and more preferably 12-13 cm; the forward voltage is 10-15 kV, and more preferably 12-13 kV.

In the present disclosure, the Method II includes the following steps:
(i) Mixing the polycaprolactone, the water-soluble compounds, the berberine with a solvent to get an electrospinning solution, and the electrospinning solution is electrospun to get the berberine nanofiber membrane;
(ii) Mixing the chitosan, the mineralized collagen with the glacial acetic acid solution, and the resulting mineralized collagen suspension is coated on the surface of the berberine nanofiber membrane and dried to get the berberine/mineralized collagen-based composite membrane.

In the present disclosure, the conditions for each operation in the step (i) are preferably consistent with those in the step (2) of the Method I, only except that the surface of the receiver is not coated with the mineralized collagen membrane during electrospinning.

In the present disclosure, the preparation method of the mineralized collagen suspension in the step (ii) is preferably consistent with that in the step (1) of the Method I.

In the present disclosure, after the berberine nanofiber membrane and the mineralized collagen suspension are obtained, the mineralized collagen suspension is coated on the surface of the berberine nanofiber membrane and dried to get the berberine/mineralized collagen-based composite membrane. In the present disclosure, the coating method is preferably spin coating. In specific examples of the present disclosure, it is preferable to spin coat 3-10 mL (most preferably 5 mL) of the mineralized collagen suspension on the surface of the berberine nanofiber membrane with an area of 9 cm×9 cm.

The present disclosure has no special requirements on the drying conditions, and any drying conditions well known to persons skilled in the art can be used.

The present disclosure also provides an application of the berberine/mineralized collagen-based composite membrane of the above solution or the berberine/mineralized collagen-based composite membrane prepared by the preparation method of the above solution in the preparation of drugs for bone repair. In the present disclosure, the berberine/mineralized collagen-based composite membrane is preferably used as membrane materials for osteogenesis. In use, the berberine/mineralized collagen-based composite membrane of the present disclosure is only required to be covered on the surface of bone defects.

Example 1

(1) Under magnetic stirring, chitosan (with a molecular weight of 12-16 kDa) was dissolved in a glacial acetic acid solution of 1 wt %, into which was then added the mineralized collagen for ultrasonic treatment and stirring successively to get a mineralized collagen suspension, where the mass fraction of chitosan was 2%, and the mass fraction of the mineralized collagen was 0.8%;

5 mL of the resulting mineralized collagen suspension was poured into a plastic watch-glass with a diameter of 10 cm, spread out and then dried in an oven at 37° C. for 2 h to get a mineralized collagen membrane, where in the resulting mineralized collagen membrane, the mass fraction of chitosan was 71.43%, and the mass fraction of the mineralized collagen was 28.57%;

(2) Berberine was dissolved in a mixed solvent of trichloromethane and methanol (the volume ratio of trichloromethane to methanol was 3:1) to get a berberine solution, then polycaprolactone was dissolved in the berberine solution to get a polycaprolactone-berberine solution where the mass fraction of polycaprolactone was 10%; polyvinylpyrrolidone was dissolved in the berberine solution to get a polyvinylpyrrolidone-berberine solution where the mass fraction of polyvinylpyrrolidone was 30%; the polycaprolactone-berberine solution and the polyvinylpyrrolidone-berberine solution were mixed at a volume ratio of 7:3, into which was then added berberine to get the electrospinning solution, where the concentration of berberine was 10 μmol/L;

(3) An injector was used to suck the electrospinning solution, then the injector was placed on the ejector of the electrospinning device, the mineralized collagen membrane was coated on the surface of the receiver, and then the electrodes were connected to start electrospinning; the model of the needle used for electrospinning is 20 G, and the receiver was a steel sheet coated with aluminum foil and had an area of 20 cm×30 cm, and the volume of solution used for electrospinning each time was 10 mL; the parameters for electrospinning were: the liquid flow rate was 0.05 mm/min, the receiving distance was 13 cm, and the forward voltage was 13 kV, finally getting the berberine/mineralized collagen-based composite membrane, where, in the resulting berberine nanofiber membrane, the mass fraction of berberine was 0.002%, the mass fraction of polycaprolactone was 43.749%, and the mass fraction of polyvinylpyrrolidone was 56.249%.

According to the concentration of berberine in the electrospinning solution, the resulting berberine/mineralized collagen-based composite membrane was remarked as CF-NFS-10.

Example 2

Conditions were the same as those in Example 1 only except that the concentration of berberine in the electrospinning solution was changed to 5 μmol/L.

Example 3

Conditions were the same as those in Example 1 only except that the concentration of berberine in the electrospinning solution was changed to 30 μmol/L.

Example 4

Conditions were the same as those in Example 1 only except that the concentration of berberine in the electrospinning solution was changed to 50 μmol/L.

Example 5

Conditions were the same as those in Example 1 only except that the mass fraction of chitosan in the mineralized collagen suspension was changed to 3%, and the mass fraction of the mineralized collagen was changed to 0.4%.

Example 6

Conditions were the same as those in Example 1 only except that the mass fraction of chitosan in the mineralized collagen suspension was changed to 6%, and the mass fraction of the mineralized collagen was changed to 0.2%.

Example 7

(1) A mineralized collagen suspension was prepared by the same method as that used in Example 1;
(2) A berberine nanofiber membrane was prepared by an electrospinning method, the specific conditions of which were consistent with those used in Example 1 only except that the receiver was not coated with the mineralized collagen membrane;
(3) 5 mL of the mineralized collagen suspension was spin coated on the surface of the berberine nanofiber membrane with an area of 9 cm×9 cm, and dried to get the berberine/mineralized collagen-based composite membrane.

Comparative Example 1

Conditions were the same as those in Example 1 only except that no berberine was added in the preparation of the electrospinning solution, and the resulting berberine/mineralized collagen-based composite membrane was remarked as CF-NFS-0.

Comparative Example 2

Conditions were the same as those in Example 1 only except that the concentration of berberine in the electrospinning solution was changed to 1 μmol/L, and the resulting berberine/mineralized collagen-based composite membrane was remarked as CF-NFS-1.

Comparative Example 3

Conditions were the same as those in Example 1 only except that the concentration of berberine in the electrospinning solution was changed to 100 μmol/L, and the resulting berberine/mineralized collagen-based composite membrane was remarked as CF-NFS-100.

Characterization of the Berberine Nanofiber Membrane:

FIG. 1 is a scanning electron micrograph of the berberine nanofiber membrane prepared in example 7, where the left panel is a scanning electron micrograph at a scale of 5 and the right panel is a scanning electron micrograph at a scale of 1 It can be seen from FIG. 1 that the resulting berberine electrospinning membrane has a 3D fiber structure with uniform distribution, the fibers are even in thickness without beads and free of adhesion, and their diameters are mainly in a range of 700-800 nm.

Figure 2:
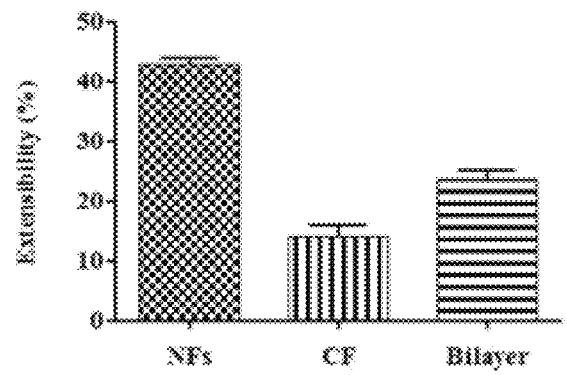
FIG. 2 is a diagram showing the ductility test results of the berberine/mineralized collagen-based composite membrane, the mineralized collagen membrane and the berberine nanofiber membrane.
Figure 3:
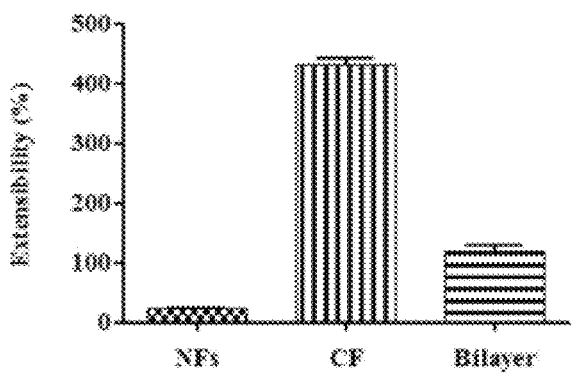
FIG. 3 is a diagram showing the Young's modulus test results of the berberine/mineralized collagen-based composite membrane, the mineralized collagen membrane and the berberine nanofiber membrane.
Figure 4:
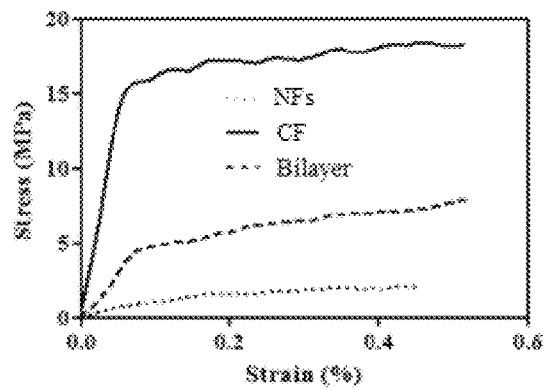
FIG. 4 shows the stress-strain curve of the berberine/mineralized collagen-based composite membrane, the mineralized collagen membrane and the berberine nanofiber membrane.

Test on Extensibility:

The berberine/mineralized collagen-based composite membrane (remarked as Bilayer) and the mineralized collagen membrane (remarked as CF) prepared in Example 1 and the berberine nanofiber membrane (remarked as NFs) prepared in Example 7 were tested for their ductility, Young's modulus and stress-strain curve, with the results being shown in FIGS. 2-4. FIG. 2 is a diagram showing the ductility test results of the berberine/mineralized collagen-based composite membrane, the mineralized collagen membrane and the berberine nanofiber membrane; FIG. 3 is a diagram showing the Young's modulus test results of the berberine/mineralized collagen-based composite membrane, the mineralized collagen membrane and the berberine nanofiber membrane; and FIG. 4 shows the stress-strain curve of the berberine/mineralized collagen-based composite membrane, the mineralized collagen membrane and the berberine nanofiber membrane. It can be seen from FIGS. 2-4 that, after the berberine nanofiber membrane is combined with the mineralized collagen membrane, the extensibility of the resulting composite membrane is between those of the berberine nanofiber membrane and the mineralized collagen membrane.

Test on Osteogenic Properties:

Osteogenic properties were tested through MTT experiments, in which the cells used were MC3T3-E1 (mouse embryonic osteoblast precursor cells), and the testing steps were as below: MC3T3-E1 cells in exponential growth period were cultured with 10% fetal calf serum to formulate a cell suspension, which was added into a culture plate for cultivation. Cell counting and plating were conducted in advance, and extract liquids were prepared by adding 15 mg drugs per mL of the culture medium. The drugs used were CF-NFS-0, CF-NFS-1, CF-NFS-10 and CF-NFS-0. The group without drugs (Control) was used as the blank control, and the group only with the drug berberine (Berberine) was used as the positive control.

Figure 5:
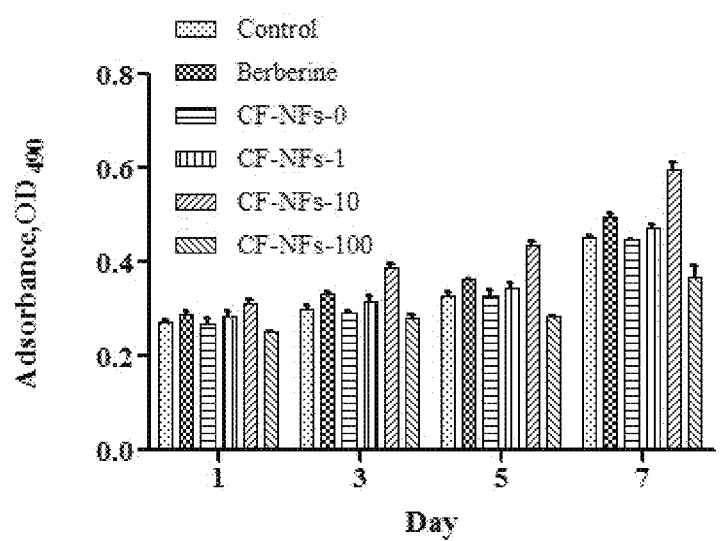
FIG. 5 is a diagram showing the test results on the osteogenic properties of the berberine/mineralized collagen-based composite membrane.

Taking MC3T3-E1 cells as the observation subjects, the above prepared extract liquids were respectively added and the profiles of cell proliferation were detected by a 4-methyl thiazolyl tetrazolium (MTT) method on day 1, day 3, day 5 and day 7 after administration. Cell viabilities were expressed by the optical densities at 490 nm ($OD_{490}$), with the results shown in FIG. 5. FIG. 5 is a diagram showing the test results on the osteogenic properties of the berberine/mineralized collagen-based composite membrane.

It can be seen from FIG. 5 that, compared with the control group and the drug group, the CF-NFS-10 group can promote the proliferation of cells most significantly; the effect of CF-NFS-0 group was comparative with that of the group without drugs; the CF-NFS-1 group has unobvious effect on promoting the proliferation of cells, and the CF-NFS-100 group even inhibited the proliferation of cells. The results showed that, the content of berberine in the berberine/mineralized collagen-based composite membrane as provided in the present disclosure is appropriate for significantly promoting the proliferation of osteoblasts, and the effects are superior to that of the drug. When the content of berberine is lower or higher than the range of the present disclosure, the effects on promoting the proliferation of cells are not satisfactory or it may inhibit the proliferation of osteoblasts.

The berberine/mineralized collagen-based composite membranes prepared in examples 2-7 were all subjected to the same tests on osteogenic properties, showing that they all have significant effects on promoting the proliferation of osteoblasts, and the effects are all superior to that of the drug.

The foregoing is only preferable implementation of the present disclosure. It should be noted to persons with ordinary skills in the art that several improvements and modifications can be made without deviating from the principle of the present disclosure, which are also considered as the protection scope of the present disclosure.

What is claimed is:

1. A preparation method of a berberine/mineralized collagen-based composite membrane comprising the following steps:
   (1) mixing chitosan and mineralized collagen with a glacial acetic acid solution to obtain a resulting mineralized collagen suspension;
   (2) mixing polycaprolactone, water-soluble compounds, and berberine with a solvent to obtain an electrospinning solution; and
   (3) casting the resulting mineralized collagen suspension obtained in step (1) into a film to obtain a mineralized collagen membrane, and electrospinning the electrospinning solution obtained in step (2) and receiving resulting electrospun fibers on the mineralized collagen membrane to obtain the berberine/mineralized collagen-based composite membrane;
   or electrospinning the electrospinning solution obtained in step (2) to obtain a berberine nanofiber membrane, coating the resulting mineralized collagen suspension obtained in step (1) on the berberine nanofiber membrane, and drying the coated berberine nanofiber membrane to obtain the berberine/mineralized collagen-based composite membrane;

wherein in the berberine/mineralized collagen-based composite membrane, the berberine nanofiber membrane comprises components of the following mass fractions: 20-65 wt % of polycaprolactone, 18-80 wt % of water-soluble compounds, and berberine≤0.1 wt % based on the mass of the berberine nanofiber membrane; and the mineralized collagen membrane comprises components of the following mass fractions: 15-90 wt % of chitosan, and 10-85 wt % of mineralized collagen based on the mass of the mineralized collagen membrane;

the mixing processes in step (2) are as below: berberine is dissolved in the solvent to get a berberine solution, then polycaprolactone and the water-soluble compounds are respectively dissolved in the berberine solution to get a polycaprolactone-berberine solution and a water-soluble compound-berberine solution; the polycaprolactone-berberine solution and the water-soluble compound-berberine solution are mixed to get the electrospinning solution; and wherein the mass concentration of polycaprolactone in the polycaprolactone-berberine solution is 5-15%; the mass concentration of the water-soluble compounds in the water-soluble compound-berberine solution is 10-30%; the volume ratio of the polycaprolactone-berberine solution to the water-soluble compound-berberine solution is 7:(2-4); the concentration of berberine in the electrospinning solution is 5-50 μmol/L; the solvent is a mixed solvent of trichloromethane and methanol.

2. The preparation method according to claim 1, wherein, the diameter of the fibers in the berberine nanofiber membrane is 700-800 nm.

3. The preparation method according to claim 1, wherein, the thickness of the berberine nanofiber membrane is 0.1-0.4 mm, and the thickness of the mineralized collagen membrane is 0.1-0.4 mm.

4. The preparation method according to claim 1, wherein, the chitosan has a molecular weight of 12-50 kDa.

5. The preparation method according to claim 1, wherein, in the mineralized collagen suspension of step (1), the mass fraction of chitosan is 0.5-6%, and the mass fraction of the mineralized collagen is 0.1-2%.

6. The preparation method according to claim 1, wherein, the method for casting into a film in step (3) is as below: the mineralized collagen suspension is poured into a mould and dried to get the mineralized collagen membrane; the drying temperature is 25-45° C., and the time is 2-5 h.

7. The preparation method according to claim 1, wherein the volume ratio of trichloromethane to methanol in the mixed solvent is (2-4):1.

8. The preparation method according to claim 1, wherein, in step (3), the parameters for electrospinning comprise: the liquid flow rate is 0.01-0.1 mm/min, the receiving distance is 10-15 cm, and the forward voltage is 10-15 kV.

* * * * *